(12) United States Patent
Kuo et al.

(10) Patent No.: US 8,148,420 B2
(45) Date of Patent: Apr. 3, 2012

(54) **USE OF NOVEL COMPOUNDS FROM FRUITING BODY OF *ANTRODIA CAMPHORATA* FOR STIMULATING IMMUNE RESPONSE**

(75) Inventors: Yueh-Hsiung Kuo, Taipei (TW); Bi-Fong Lin, Taipei (TW)

(73) Assignee: Well Shine Biotechnology Development Co., Ltd., Taipei (TW)

( * ) Notice: Subject to any disclaimer, the term of this patent is extended or adjusted under 35 U.S.C. 154(b) by 0 days.

(21) Appl. No.: 12/956,897

(22) Filed: Nov. 30, 2010

(65) Prior Publication Data

US 2011/0077282 A1 Mar. 31, 2011

Related U.S. Application Data

(62) Division of application No. 12/275,874, filed on Nov. 21, 2008, now Pat. No. 7,932,285.

(51) Int. Cl.
*A61K 31/4015* (2006.01)
*A61K 31/341* (2006.01)
*A61K 31/216* (2006.01)

(52) U.S. Cl. .................. 514/425; 514/473; 514/533

(58) Field of Classification Search .................. None
See application file for complete search history.

(56) References Cited

OTHER PUBLICATIONS

Chien et al., J. Agric. Food Chem. 2008, 56, 7017-7022.*
Singh et al., Clinical Chemistry, 2005, 51:12.*
Cheng et al., Tetrahedron, vol. 64, No. 19, 2008.*
Wu et al. J. Nat. Prod. 2008, 71, pp. 1258-1261.*
Chen, et al, "*Effects of Triterpenoid-Rich Extracts of Ganoderma tsugae on Airway Hyperreactivity and Th2 Responses in Vvivo*", Int. Arch Allergy Immunol 2007; 143:21-30.
Kantar, et al, "*Plasma Concentrations of Granulocyte-Macrophage Colony-Stimulating Factor and Interleukin-6 in Septic and Healthy Preterms*", Eur. J. Pediatr. (2000), 159: 156-157.
Pathan, et al, "*Role of Interleukin 6 in Myocardial Dysfunction of Meningococcal Septic Shock*", The Lancet, vol. 363, Jan. 17, 2004: 203-209.
Shen, et al, "*New Ergostane and Lanostane From Antrodia camphorata*", J. Chin. Med 14(4): 247-258, 2003.
Singh, et al, "*Development of an In Vitro Screening Assay to Test the Antiinflammatory Properties of Dietary Supplements and Pharmacologic Agents*" Clinical Chemistry 51:12 2252-2256 (2005).

* cited by examiner

*Primary Examiner* — Rebecca Anderson
*Assistant Examiner* — Alicia L Otton
(74) *Attorney, Agent, or Firm* — Occhiuti Rohlicek & Tsao LLP

(57) ABSTRACT

Methods of stimulating immune response or treating an inflammatory disorder with one of a number of the compounds disclosed herein or a pharmaceutically acceptable salt thereof.

2 Claims, No Drawings

USE OF NOVEL COMPOUNDS FROM FRUITING BODY OF *ANTRODIA CAMPHORATA* FOR STIMULATING IMMUNE RESPONSE

CROSS-REFERENCE TO RELATED APPLICATION

This application is a divisional of U.S. patent application Ser. No. 12/275,874, filed on Nov. 21, 2008. The content of the prior application is hereby incorporated by reference in its entirety.

FIELD OF THE INVENTION

The present invention pertains to novel immunostimulatory and anti-inflammatory compounds from *Antrodia camphorata*.

BACKGROUND OF THE INVENTION

*Antrodia camphorata*, which is equal to *Taiwanofungus camphorata*, is native to Taiwan. Its fruiting body is a very rare and expensive mushroom that grows slowly in the wild and it is difficult to cultivate in the greenhouse. The fruiting body of *A. camphorata* has traditionally been used as an herbal medicine in Taiwan and is commonly known by name "jang-jy" or "niu-chang-chih" (Shen C. C. et al., *J. Chin. Med.* 2003, 14, 247-258).

Naturally, it grows on the inner heartwood wall of *Cinnamomun kanehirai* Hay (Lauraceae), an endemic and endangered species in Taiwan. The wild-type fruiting body contains fatty acids, lignans, phenyl derivatives, sesquiterpenes, steroids, and triterpenoids (Shen C. C. et al., ut supra). In traditional herbal medicine, *A. camphorata* fruiting bodies have been utilized as treatment for food and drug intoxications, diarrhea, abnormal pains, hypertension, itchy skin and liver cancer.

BRIEF SUMMARY OF THE INVENTION

The present invention is based on the unexpected finding that certain compounds isolated from *A. camphorata* exhibit anti-inflammation and/or immunomodulatory (e.g., immunostimulatory) effect. The compounds of the present invention include some new maleic acid and succinic acid derivatives isolated from the fruiting body of *A. camphorata* in a solid culture.

In one aspect, the invention relates an isolated compound or a pharmaceutically acceptable salt thereof. The isolated compound is of a formula which is selected from the group consisting of

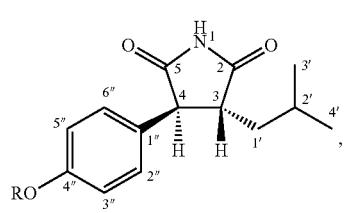

Formula I

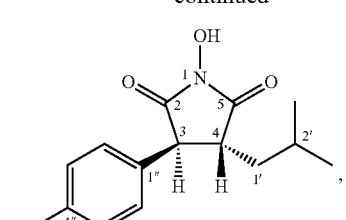

Formula II

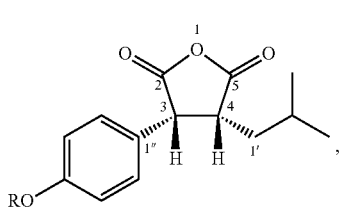

Formula III

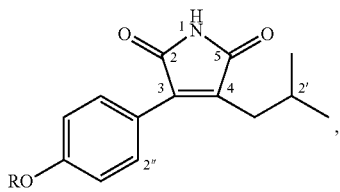

Formula IV

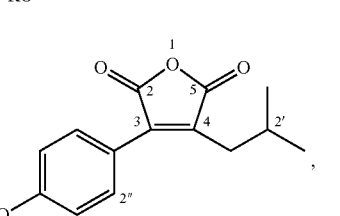

Formula V

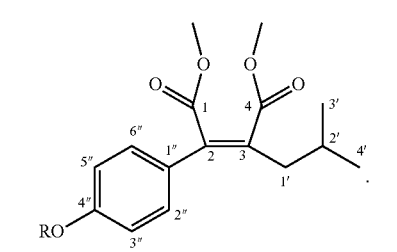

, and

Formula VI

In Formulas I-VI, each R independently is H, $C_{1-4}$alkyl,

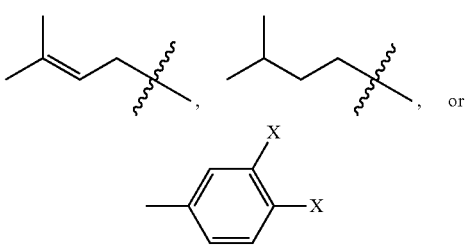

in which each X independently is H, OH, OR, $NH_2$, or NHR', R' being alkyl or acyl.

One subset of the above isolated compounds include trans-3-isobutyl-4-[4-(3-methyl-2-butenyloxy)phenyl]pyrrolidine-2,5-dione, trans-1-hydroxy-3-(4-hydroxyphenyl)-4-isobutylpyrrolidine-2,5-dione, cis-3-(4-hydroxyphenyl)-4-isobutyldihydrofuran-2,5-dione, 3-(4-hydroxyphenyl)-4- isobutyl-1H-pyrrole-2,5-dione, 3-(4-hydroxyphenyl)-4-isobutylfuran-2,5-dione, or dimethyl 2-(4-hydroxyphenyl)-3-isobutylmaleate.

The term "isolated compound" used herein refers to a compound that is prepared by a synthetic method or enriched from a natural source (e.g., *Antrodia camphorata*). For example, an isolated compound is a preparation that contains 40% of a compound of interest by dry weight. Purity of an isolated compound can be measured by, e.g., column chromatography, mass spectrometry, high performance liquid chromatography (HPLC), NMR, or any other suitable methods.

The term "alkyl" refers to a straight or branched monovalent hydrocarbon containing 1-20 carbon atoms (e.g., $C_{1-10}$). The term acyl refers to —C(O)R in which R can be alkyl or other groups such as alkenyl, alkynyl, cycloalkyl, heterocycloalkyl, aryl, or heteroaryl.

Alkyl, alkenyl, alkynyl, cycloalkyl, heterocycloalkyl, aryl, and heteroaryl mentioned above include both substituted and unsubstituted moieties. Possible substituents on cycloalkyl, heterocycloalkyl, aryl, and heteroaryl include, but are not limited to, $C_1$-$C_{10}$ alkyl (e.g., trifluoromethyl), $C_2$-$C_{10}$ alkenyl, $C_2$-$C_{16}$ alkynyl (e.g., arylalkynyl), $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl (e.g., haloaryl or aryl substituted with halo), aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl can also be fused with each other.

The pharmaceutically acceptable salt of the above mentioned isolated compound, for example, can be formed between an anion and a positively charged group (e.g., amino) on the isolated compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on the isolated compound. Suitable cations include sodium ion, potassium ion, magnesium ion, calcium ion, and an ammonium cation such as tetramethylammonium ion. The salt also includes those salts containing quaternary nitrogen atoms.

The above compounds may contain one or more asymmetric centers or a non-aromatic double bond. Thus, they can occur as racemates and racemic mixtures, single enantiomers, individual diastereomers, diastereomeric mixtures, and cis- or trans-isomeric forms. All such isomeric forms are contemplated.

In another aspect, this invention relates to a method for stimulating immune responses. The method includes administering to a subject in need thereof an effective amount of one or more isolated compounds or their pharmaceutically acceptable salts described above.

In a further aspect, this invention relates to a method for treating an inflammatory disease. The method includes administering to a subject in need thereof an effective amount of one or more isolated compounds or their pharmaceutically acceptable salts described above. Examples of inflammatory disorders include but are not limited to autoimmune diseases, asthma, chronic inflammation, allergies, and cancer.

Also within the scope of this invention is a pharmaceutical composition (including an *A. camphorata* extract) containing one or more of the above-described isolated compounds or their salts for use in stimulating immune responses and/or treating an inflammatory disorder, as well as this therapeutic use and use of the compounds or their salts for the manufacture of a medicament for treating an inflammatory disorder and/or stimulating immune responses.

The details of one or more embodiments of the invention are set forth in the description below. Other features, objects, and advantages of the invention will be apparent from the description and from the claims.

DETAILED DESCRIPTION OF THE INVENTION

The present invention relates to a compound or a pharmaceutically acceptable salt thereof, which is isolated, e.g., from *A. camphorata*, and its use for treating inflammatory disorders and/or stimulating immune responses.

The compound of the invention can either be isolated from a natural source, such as the fruiting body of *Antrodia camphorata*, or be chemically synthesized. To obtain the compound of the present invention from the fruiting body of *Antrodia camphorata*, a conventional extraction method can be used. In one example of the invention, the fruiting body of a *Ganoderma*-like fungus (e.g., *Antrodia camphorata*) were collected, dried, and soaked in an alcohol (e.g., methanol, ethanol, or a mixture thereof) for a suitable period of time (e.g., at least four day). After removing the alcohol via, e.g., vacuum, water was added to the residue to form a suspension. The suspended phase was partitioned with an appropriate polar solvent (e.g., EtOAc). The polar solvent layer was condensed into a black syrup, via e.g. evaporation. Then, the individual component in the syrup was separated via any form of purification, such as column chromatography with, e.g., n-hexane, EtOAc, and MeOH. The final compound was then characterized by $^1$H and $^{13}$C NMR. Six newly discovered compounds were obtained: trans-3-Isobutyl-4-[4-(3-methyl-2-butenyloxy)phenyl]pyrrolidine-2,5-dione (compound 1), trans-1-Hydroxy-3-(4-hydroxyphenyl)-4-isobutylpyrrolidine-2,5-dione (compound 2), cis-3-(4-Hydroxyphenyl)-4-isobutyldihydrofuran-2,5-dione (compound 3), 3-(4-Hydroxyphenyl)-4-isobutyl-1H-pyrrole-2,5-dione (compound 4), 3-(4-Hydroxyphenyl)-4-isobutylfuran-2,5-dione (compound 5) and dimethyl 2-(4-hydroxyphenyl)-3-isobutylmaleate (compound 6).

Synthetic chemistry transformations useful in synthesizing applicable compounds of the invention are described, for example, in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof. A compound thus synthesized can be further purified by flash column chromatography, high performance liquid chromatography, crystallization, or any other suitable methods.

Also within the scope of this invention are (1) a pharmaceutical composition that contains an effective amount of one or more compounds or their salts of this invention and a pharmaceutically acceptable carrier, (2) a method for treating an inflammatory disorder by administering to a subject (e.g., a patient) in need of this treatment an effective amount of such compound or its pharmaceutically acceptable salt, and (3) a method for stimulating immune responses by administering to a subject (e.g., hosts having a weak immune system such as infants, AIDS patients, leukemia patients, and organ transplant recipients) in need of this treatment an effective amount of such compound or its pharmaceutically acceptable salt.

As used herein, the term "treating" refers to administering an isolated compound or its salt to a subject that has an inflammatory disorder, or has a symptom of or a predisposition toward such a disorder, with the purpose to cure, heal, alleviate, relieve, alter, remedy, ameliorate, improve, or affect the above-described disorder, the symptoms of or the predisposition toward it. The term "an effective amount" refers to the amount of the active agent that is required to confer the intended therapeutic effect in the subject. For example, an effective amount of the compound or the pharmaceutically acceptable salts thereof for modulating immunity is an amount sufficient to reduce or increase the production of cytokines (e.g. TNF-$\alpha$, IL-6) by immune cells, such as macrophages. Effective amounts may vary, as recognized by those skilled in the art, depending on route of administration, excipient usage, and the possibility of co-usage with other agents.

To practice the method of this invention, the above-described pharmaceutical composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil, castor oil, corn oil, cottonseed oil, sesame oil, coconut oil, or peanut oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions, syrups, elixirs, suspensions (e.g., aqueous suspensions), dispersions, and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. An isolated compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. Compatible carriers may include, but are not limited to: saline, buffered saline, dextrose, water, glycerol, ethanol and combinations thereof. Stabilizing carriers, for example, can form more soluble complexes with the isolated compounds. Solubilizing agents can be utilized as pharmaceutical carriers for delivery of the active compounds. Examples of other carriers include colloidal silicon dioxide, magnesium stearate, sodium lauryl sulfate, and D&C Yellow #10.

The isolated compounds described above can be preliminarily screened for their efficacy in modulating immunity (e.g., stimulating immune responses) or treating inflammatory diseases by an in vitro assay and then confirmed by animal experiments and clinic trials. Other methods will also be apparent to those of ordinary skill in the art.

To determine via in vitro assay immunomodulatory effects of the compound of the present invention, a macrophage cell line, RAW264.7 cell model for cytokine production can be used. Macrophages are cells in the tissues, which originate from specific white blood cells called monocyte. They are part of the innate immune system, recognizing, engulfing, and destroying many potential pathogens including bacterial, pathogenic protozoa, fungi, and helminths. As secretory cells, activated macrophages are vital to the regulation of immune responses and the development of inflammation. They churn out an amazing array of powerful chemical substances (monokines) including enzymes, complement proteins, and regulatory factors such as IL-$\beta$, TNF-$\alpha$, IL-6, and nitric oxide (NO). Macrophage cell lines, such as murine RAW264.7 and human THP-1, have been proposed as rapid in vitro screening methods to test the immunomodulatory effect agents (Singh, U. et al., *Clin. Chem.* 2005, 51, 2252-2256). As described in the following examples, the compounds of the invention were proven to induce the spontaneously production of TNF-$\alpha$ (see Example 3); and the compounds were proved to inhibit the spontaneously production of IL-6 (see Example 4). Accordingly, due to their excellent immunomodulatory activity in vitro, the compounds of this invention or the pharmaceutically acceptable salts thereof can be used as an active ingredient in pharmaceutical compositions for stimulating immunity or anti-inflammation treatment.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Material and Method

General Experimental Procedures

Melting points were determined with a Yanagimoto micromelting point apparatus. IR spectra were recorded on a Perkin-Elmer 983G spectrophotometer. $^1$H, $^{13}$C and DEPT spectra were acquired on a Bruker DMX-400 spectrometer, and two-dimensional NMR spectra were acquired on a Bruker DMX-500 spectrometer. EIMS, UV, and specific rotations were determined using a JEOL JMS-HX 300, Hitachi S-3200 spectrometer, and JASCO DIP-180 digital polarimeter, respectively. Extracts were initially fractionated on silica gel (Merck 70-230 mesh, 230-400 mesh, ASTM) and then purified with a semi-preparative normal-phase HPLC column (250×10 mm, 7 µm, LiChrosorb Si 60) on an LDC Analytical-III system.

Plant Material

The solid cultural fruiting bodies of A. camphorata were identified and provided by Well Shine Biotechnology Development, Taipei, Taiwan. A voucher specimen was deposited at Well Shine Biotechnology. Development Co. Ltd.

Statistical Analysis

The data are expressed as the means±standard deviation of three independent experiments. The significance of difference between each treatment was analyzed by unpaired Student's t test using Strategic Application Software (SAS Windows version 8.2; SAS Institute Inc., Cary, N.C.) throughout the study. Data are expressed as mean±SD. Values at p<0.05 are considered to be significant.

EXAMPLE 1

Isolation and Characterization of Compounds

The fruiting bodies of solid culture A. camphorata (3.0 kg) were extracted with MeOH (12 L) by maceration at room temperature (4 days×3). After removal of MeOH in vacuum, $H_2O$ was added to bring the total volume to 1 L. This suspended phase was partitioned with EtOAc (1 L×3). Evaporation of the combined EtOAc layers afforded black syrup (212 g). The EtOAc fraction (200 g) was chromatographed on a silica gel column (10×70 cm, Merk 70-230 mesh) using n-hexane, EtOAc, and MeOH of increasing polarity as eluent to obtain 9 fractions: fr. 1 [8000 mL, n-hexane/EtOAc (19:1)], fr. 2 [7000 mL, n-hexane/EtOAc (9:1)], fr. 3 [6000 mL, n-hexane/EtOAc (8:2)], fr. 4 [10000 mL, n-hexane/EtOAc (7:3)], fr. 5 [8000 mL, n-hexane/EtOAc (1:1)], fr. 6 [9000 mL, n-hexane/EtOAc (1:3)], fr. 7 (8000 mL, EtOAc), fr. 8 [7000 mL, EtOAc/MeOH (1:0], fr. 9 (6000 mL, MeOH). A liquid-liquid partition was conducted to obtain the EtOAc fraction having anti-inflammatory activity. Further fractionation on a silica gel column was preformed to obtain the fractions rich in anti-inflammatory activity, wherein the concentrations for 50% inhibition of IL-6 production by the crude extract and EtOAc fraction were tested to be 42 and 30 µg/mL, respectively. The bio-active fraction was subjected to further chemical analysis to give six new compounds from fr. 6. HPLC on a normal-phase column with n-hexane/EtOAc (4:1) as eluent, 4 mL/min, afforded compound 1 (12.5 mg), compound 2 (22.6 mg), compound 3 (6.8 mg), compound 4 (9.4 mg), compound 5 (15.0 mg), compound 6 (13.2 mg), and compound 7 (8.9 mg), respectively. These six compounds are: trans-3-Isobutyl-4-[4-(3-methyl-2-butenyloxy)phenyl]pyrrolidine-2,5-dione (compound 1), trans-1-Hydroxy-3-(4-hydroxyphenyl)-4-isobutylpyrrolidine-2,5-dione (compound 2), cis-3-(4-Hydroxyphenyl)-4-isobutyldihydrofuran-2,5-dione (compound 3), 3-(4-Hydroxyphenyl)-4-isobutyl-1H-pyrrole-2,5-dione (compound 4), 3-(4-Hydroxyphenyl)-4-isobutylfuran-2,5-dione (compound 5) and Dimethyl 2-(4-hydroxyphenyl)-3-isobutylmaleate (compound 6).

The $^1$H and $^{13}$C NMR data of the compounds of 1-6 are complied in Table 1 and Table 2.

TABLE 1

$^1$H NMR Data of Compounds 1-6 (400 MHz, 1-3, 5-6 in CDCl$_3$, 4 in CD$_3$OD)

| No. | 1 | 2 | 3 | 4 | 5 | 6 |
|---|---|---|---|---|---|---|
| 1 | 7.94 br s | | | | | |
| 2 | | | | | | |
| 3 | 2.97 dt (5.2, 5.2) | 3.68 d (5.0) | 3.59 d (11.1) | | | |
| 4 | 3.60 d (5.2) | 2.91 m | 3.17 td (11.1, 3.6) | | | |
| 5 | | | | | | |
| 1' | 1.54 m | 1.75-1.85 m 1.60 m | 1.37 m 1.70 m | 2.48 d (7.6) | 2.56 d (7.2) | 2.14 d (7.2) |
| 2' | 1.83 m | 1.75-1.85 m | 1.61 m | 1.99 m | 2.08 m | 1.70 m |
| 3' | 0.71 d (6.4) | 0.69 d (6.3) | 0.91 d (6.5) | 0.87 d (6.8) | 0.91 d (6.7) | 0.77 d (6.8) |
| 4' | 0.89 d (6.4) | 0.88 d (6.3) | 0.97 d (6.5) | 0.87 d (6.8) | 0.91 d (6.7) | 0.77 d (6.8) |
| 1" | | | | | | |
| 2", 6" | 7.10 d (8.8) | 7.17 d (8.5) | 7.20 d (8.6) | 7.43 d (9.0) | 7.54 d (8.8) | 7.09 d (8.2) |
| 3", 5" | 6.88 d (8.8) | 6.83 d (8.5) | 6.75 d (8.6) | 6.87 d (9.0) | 6.94 d (8.8) | 6.81 d (8.2) |
| 4" | | | | | | |
| 1'" | 4.47 d (6.8) | | | | | |
| 2'" | 5.46 br t (6.8) | | | | | |
| 3'" | | | | | | |
| 4'" | 1.72 s | | | | | |
| 5'" | 1.78 s | | | | | |
| 1-OC$\underline{H}_3$ | | | | | | 3.70 s |
| 4-OC$\underline{H}_3$ | | | | | | 3.80 s |

TABLE 2

$^{13}$C NMR Data of Compounds 1-6 (100 MHz, 1-3, 5-76 in CDCl$_3$, 4 in CD$_3$OD)

| No | 1 | 2 | 3 | 4 | 5 | 6 |
|---|---|---|---|---|---|---|
| 1 | | | | | | 168.3 |
| 2 | 179.2 | 172.0 | 173.3 | 172.6 | 166.4 | 137.5 |
| 3 | 48.3 | 49.7 | 53.9 | 138.7 | 140.0 | 140.1 |
| 4 | 53.8 | 44.2 | 47.5 | 138.3 | 140.2 | 169.4 |
| 5 | 177.4 | 173.0 | 174.1 | 173.5 | 165.5 | |
| 1' | 40.6 | 40.1 | 40.9 | 32.4 | 33.6 | 39.1 |
| 2' | 25.6 | 25.0 | 26.3 | 28.1 | 27.9 | 27.4 |

TABLE 2-continued $^{13}$C NMR Data of Compounds 1-6
(100 MHz, 1-3, 5-76 in CDCl$_3$, 4 in CD$_3$OD)

| No | 1 | 2 | 3 | 4 | 5 | 6 |
|---|---|---|---|---|---|---|
| 3' | 23.0 | 22.4 | 23.1 | 22.0 | 22.6 | 22.4 |
| 4' | 21.4 | 20.7 | 20.6 | 22.0 | 22.6 | 22.4 |
| 1" | 128.5 | 128.5 | 128.0 | 120.5 | 120.0 | 127.1 |
| 2", 6" | 128.7 | 129.3 | 129.5 | 131.0 | 131.3 | 130.4 |
| 3", 5" | 115.4 | 115.6 | 115.0 | 115.2 | 116.0 | 115.3 |
| 4" | 158.6 | 156.8 | 156.8 | 158.8 | 158.2 | 155.5 |
| 1''' | 64.8 | | | | | |
| 2''' | 119.4 | | | | | |
| 3''' | 138.5 | | | | | |
| 4''' | 18.2 | | | | | |
| 5''' | 25.8 | | | | | |

TABLE 2-continued $^{13}$C NMR Data of Compounds 1-6
(100 MHz, 1-3, 5-76 in CDCl$_3$, 4 in CD$_3$OD)

| No | 1 | 2 | 3 | 4 | 5 | 6 |
|---|---|---|---|---|---|---|
| 1-OCH$_3$ | | | | | | 52.4 |
| 4-OCH$_3$ | | | | | | 52.2 |

EXAMPLE 2

Immunostimulatory Effect of the Compounds

The cytokine levels in culture supernatants were measured by sandwich ELISA methods as described by Chen and Lin (Chen, M. L. et al., *Int. Arch. Allergy Immunol.* 2007, 143, 21-30). More specifically, the anti-cytokine antibodies (PharMingen, San Diego, Calif.) were coated in the 96-well plates (Nunc, Roskilde, Denmark) after overnight incubation at 4° C. and having been blocked with 1% BSA PBS buffer for 30 min. The samples and standards (recombinant mouse cytokines, PharMingen) were added to the 96-well plates for 2 hours incubation. The biotin-conjugated antibodies (biotinylated rat anti-mouse cytokine monoclonal antibodies, PharMingen) were added and incubated. After washing, streptavidin-conjugated peroxidase was added for 1 hour. The substrates, 2,2'-azino-bis-3-ethyl-benzthiazoline-6-sulfonic acid (ABTS, Sigma), were added to each well for 20 min. The plates were read in a microplate autoreader (Microplate autoreader; Bio-Tek Instruments, Winooski, Vt.) at 405 nm.

To evaluate the immunomodulatory effects of these new compounds, the in vitro production of cytokines in RAW264.7 cells were treated without or with the compounds of the invention at different concentrations for 48 hours. The supernatants were collected for TNF-α assay, and cells were collected for viability analysis by MTT method. Data are showed as means±SD of three independent experiments with triplicates of each.

As shown in Table 3, Compound 1 significantly increased spontaneous TNF-α secretion by RAW264.7 cells without affecting cell viability, suggesting that Compound 1 has the potential to activate macrophages. TNF-α levels secreted by RAW264.7 cells stimulated by 0.5~5 μg/mL of Compound 1 increased in a dose-dependent manner. These data suggest that Compound 1 stimulate macrophages to secret TNF-α without cell toxicity.

TABLE 3

The effects of compounds isolated from *A. camphorata* on viability and spontaneous TNF-α secretion in RAW264.7 macrophage cells

| Conc. (μg/mL) | Compounds | | | | | |
|---|---|---|---|---|---|---|
| | 1 | 2 | 3 | 4 | 5 | 6 |
| | Cell viability (%) | | | | | |
| 0 | 100 ± 0 | 100 ± 0 | 100 ± 0 | 100 ± 0 | 100 ± 0 | 100 ± 0 |
| 0.5 | 103 ± 2 | 106 ± 7 | 91 ± 9 | 97 ± 13 | 101 ± 7 | 100 ± 6 |
| 1 | 101 ± 3 | 100 ± 5 | 87 ± 8 | 99 ± 4 | 102 ± 5 | 99 ± 7 |
| 2 | 108 ± 6 | 100 ± 5 | 80 ± 9* | 97 ± 5 | 99 ± 6 | 102 ± 6 |
| 5 | 100 ± 10 | 94 ± 6 | 72 ± 11* | 94 ± 7 | 95 ± 9 | 95 ± 8 |
| 10 | 99 ± 7 | 90 ± 4* | 67 ± 15* | 81 ± 8* | 86 ± 8* | 96 ± 11 |
| | TNF-α (pg/mL) secretion | | | | | |
| 0 | 88 ± 45 | 88 ± 45 | 88 ± 45 | 88 ± 45 | 88 ± 45 | 88 ± 45 |
| 0.5 | 117 ± 31 | 108 ± 28 | 55 ± 2 | 91 ± 38 | 100 ± 26 | 100 ± 34 |
| 1 | 145 ± 44 | 97 ± 13 | 74 ± 7 | 83 ± 22 | 102 ± 30 | 114 ± 41 |
| 2 | 183 ± 89** | 105 ± 23 | 68 ± 7 | 105 ± 13 | 90 ± 4 | 90 ± 14 |
| 5 | 212 ± 60* | 96 ± 8 | 68 ± 26 | 118 ± 23 | 94 ± 19 | 110 ± 22 |
| 10 | 188 ± 41* | 128 ± 70 | 77 ± 35 | 104 ± 25 | 106 ± 5 | 116 ± 4 |

*$p < 0.05$;
**$0.05 < p < 0.1$; significantly different from the control (no extract treatment) group.

EXAMPLE 3

Anti-inflammation Effect of the Compounds

IL-6, a proinflammatory cytokine which is a useful marker of infection, is secreted by macrophages in many infectious and inflammatory states, including cardiac surgery, cardiogenic shock, coronary bypass and bacteria sepsis (Kantar, M. et al., *Eur. J. Pediatr.* 2000, 159, 156-157). Serum concentration of IL-6 has been reported to correlate with disease severity (Pathan, N. et al., *Lancet* 2004, 363, 203-209). The productions of IL-6 from LPS-stimulated macrophages were measured to evaluate the anti-inflammation effect of the compounds. The cells were pretreated with compounds isolated from *A. camphorata* for 30 min and then stimulated with 50 ng/mL LPS for 48 hours. The supernatants were collected for TNF-α and IL-6 assay, and the cells were collected for viability analysis by MTT method. Data are showed as means±SD.

As shown in Table 4, these compounds did not affect the viability of RAW264.7 macrophages. When the cells were stimulated with LPS, the IL-6 production was significantly decreased by compound 1 in a dose-dependent manner. The concentration required for 50% inhibition (IC$_{50}$) of IL-6 production by compound 1 was 10 μg/mL. The concentration required for 50% inhibition (IC$_{50}$) of IL-6 production by compound 1 was 10 μg/mL. Compounds 3, 4, and 6 also suppressed IL-6 production. They had IC$_{50}$ values of 17, 18, and 25 μg/mL, respectively. Compounds 2 and 5 IC$_{50}$ values of 54 and 96 μg/mL, respectively.

TABLE 4

The effects of compounds isolated from *A. camphorate* on cell viability, TNF-α and IL-6 secretion in LPS-stimulated RAW264.7 macrophage cells.

| Conc. (µg/mL) | Compounds | | | | | |
|---|---|---|---|---|---|---|
| | 1 | 2 | 3 | 4 | 5 | 6 |
| | Cell viability (%) | | | | | |
| 0 | 100 ± 0 | 100 ± 0 | 100 ± 0 | 100 ± 0 | 100 ± 0 | 100 ± 0 |
| 0.5 | 105 ± 3 | 110 ± 5* | 105 ± 6 | 105 ± 6 | 106 ± 4* | 108 ± 6 |
| 1 | 106 ± 4 | 111 ± 6* | 104 ± 6 | 103 ± 5 | 105 + 2* | 107 ± 7 |
| 5 | 105 ± 3 | 111 ± 8* | 99 ± 3 | 97 ± 5 | 102 ± 2 | 106 ± 9 |
| 10 | 102 ± 4 | 109 ± 2* | 91 ± 4* | 92 ± 8 | 100 ± 3 | 102 ± 10 |
| | TNF-α (ng/mL) secretion | | | | | |
| 0 | 3.81 ± 0.93 | 3.81 ± 0.93 | 3.81 ± 0.93 | 3.81 ± 0.93 | 3.81 ± 0.93 | 3.81 ± 0.93 |
| 0.5 | 3.69 ± 0.39 | 3.34 ± 0.58 | 3.17 ± 0.70 | 2.98 ± 0.24 | 3.44 ± 0.31 | 3.61 ± 0.22 |
| 1 | 3.92 ± 0.39 | 4.04 ± 0.46 | 3.64 ± 0.84 | 3.22 ± 0.35 | 4.06 ± 1.14 | 3.70 ± 0.50 |
| 5 | 3.68 ± 0.25 | 4.76 ± 0.65 | 3.88 ± 0.37 | 3.72 ± 0.23 | 4.67 ± 1.09 | 3.80 ± 0.53 |
| 10 | 3.65 ± 0.17 | 3.66 ± 0.67 | 3.90 ± 0.10 | 3.12 ± 0.61 | 3.63 ± 0.58 | 3.32 ± 0.30 |
| | IL-6 (pg/mL) secretion | | | | | |
| 0 | 238 ± 86 | 238 ± 86 | 238 ± 86 | 238 ± 86 | 238 ± 86 | 238 ± 86 |
| 0.5 | 213 ± 88 | 216 ± 102 | 214 ± 82 | 194 ± 81 | 221 ± 102 | 235 ± 106 |
| 1 | 211 ± 99 | 224 ± 110 | 234 ± 109 | 257 ± 40 | 227 ± 94 | 215 ± 89 |
| 5 | 144 ± 64 | 210 ± 96 | 185 ± 76 | 195 ± 83 | 225 ± 68 | 209 ± 89 |
| 10 | 103 ± 61* | 191 ± 68 | 147 ± 53** | 169 ± 63** | 215 ± 56 | 179 ± 91 |
| $IC_{50}$ (µg/mL) | 10 | 54 | 17 | 18 | 96 | 25 |

*$p < 0.05$;
**$0.05 < p < 0.1$; significantly different from the control (no extract treatment) group.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of stimulating production of TNF-α or inhibiting production of IL6, comprising administering to a subject in need thereof an effective amount of an isolated compound or a pharmaceutically acceptable salt thereof, wherein the compound is selected from the group consisting of trans-3-isobutyl-4-[4-(3-methyl-2-butenyloxy)phenyl]pyrrolidine-2,5-dione, trans-1-hydroxy-3-(4-hydroxyphenyl)-4-isobutylpyrrolidine-2,5-dione, cis-3-(4-hydroxyphenyl)-4-isobutyldihydrofuran-2,5-dione, 3-(4-hydroxyphenyl)-4-isobutyl-1H-pyrrole-2,5-dione, and dimethyl 2-(4-hydroxyphenyl)-3-isobutylmaleate.

2. The method of claim 1, wherein the compound is trans-3-isobutyl-4-[4-(3-methyl-2-butenyloxy)phenyl]pyrrolidine-2,5-dione.

* * * * *